(12) United States Patent
Swaney et al.

(10) Patent No.: US 12,714,760 B2
(45) Date of Patent: Aug. 25, 2026

(54) STERILIZATION DEVICE

(71) Applicant: Hai Solutions, Inc., Carlsbad, CA (US)

(72) Inventors: Paul Swaney, Carlsbad, CA (US); Adnan Abbas, Carlsbad, CA (US)

(73) Assignee: HAI Solutions, Inc., Carlsbad, CA (US)

( * ) Notice: Subject to any disclaimer, the term of this patent is extended or adjusted under 35 U.S.C. 154(b) by 521 days.

(21) Appl. No.: 16/804,585

(22) Filed: Feb. 28, 2020

(65) Prior Publication Data

US 2021/0023247 A1 Jan. 28, 2021

Related U.S. Application Data

(63) Continuation of application No. 16/168,730, filed on Oct. 23, 2018, now Pat. No. 10,610,609.

(60) Provisional application No. 62/575,899, filed on Oct. 23, 2017.

(51) Int. Cl.
*A61L 2/10* (2026.01)
*A61L 2/28* (2006.01)
*A61L 103/15* (2026.01)

(52) U.S. Cl.
CPC .................. *A61L 2/10* (2013.01); *A61L 2/28* (2013.01); *A61L 2103/15* (2026.01); *A61L 2202/122* (2013.01)

(58) Field of Classification Search
CPC ............................... A61L 2/10; A61L 2202/24
See application file for complete search history.

(56) References Cited

U.S. PATENT DOCUMENTS

| | | | |
|---|---|---|---|
| 6,590,698 B1 | 7/2003 | Ohtsuki et al. | |
| 7,390,417 B2 | 6/2008 | Kuhlmann et al. | |
| 8,633,454 B2 | 1/2014 | Durkin | |
| 9,433,694 B1 | 9/2016 | Hsu | |
| 9,764,126 B2 | 9/2017 | Tornblom | |
| 10,610,609 B2 | 4/2020 | Swaney et al. | |
| 2002/0088945 A1 | 7/2002 | Matschke | |
| 2003/0017073 A1 | 1/2003 | Eckhardt et al. | |
| 2004/0034398 A1 | 2/2004 | Eckhardt et al. | |
| 2004/0200783 A1 | 10/2004 | Castellini | |
| 2007/0072153 A1 | 3/2007 | Gross et al. | |
| 2007/0176117 A1 | 8/2007 | Redmond et al. | |
| 2007/0295213 A1 | 12/2007 | Okamoto et al. | |
| 2008/0095661 A1* | 4/2008 | Kohler | C02F 1/487 422/119 |

(Continued)

FOREIGN PATENT DOCUMENTS

| | | |
|---|---|---|
| CA | 2676695 A1 | 8/2008 |
| CN | 202724294 U | 2/2013 |

(Continued)

OTHER PUBLICATIONS

International Search Report and Written Opinion mailed Mar. 28, 2019 for International Application Serial No. PCT/US2018/057138 filed on Oct. 23, 2018.

(Continued)

*Primary Examiner* — Donald R Spamer
(74) *Attorney, Agent, or Firm* — K&L Gates LLP; Brian J. Novak; Giorgios N. Kefallinos

(57) ABSTRACT

Described herein generally are sterilization devices that can allow sterilization of luminal connection ports. Methods of using these devices are also described.

26 Claims, 5 Drawing Sheets

(56) References Cited

U.S. PATENT DOCUMENTS

2008/0169249 A1 7/2008 Ter Stege
2008/0208297 A1 8/2008 Gertner et al.
2009/0117001 A1 5/2009 Hyde et al.
2009/0314956 A1 12/2009 Long
2010/0178200 A1 7/2010 Walker et al.
2010/0324505 A1* 12/2010 Levenson ......... A61M 25/0097 250/435
2011/0085936 A1 4/2011 Haytman et al.
2011/0104017 A1 5/2011 Migliore et al.
2011/0126370 A1 6/2011 Reuben
2012/0321509 A1* 12/2012 Bak ....................... A61M 39/16 250/435
2013/0004479 A1 1/2013 DiCosimo et al.
2013/0045133 A1 2/2013 Maguire
2013/0062534 A1 3/2013 Cole
2013/0177865 A1 7/2013 Ostler
2013/0273493 A1 10/2013 Noui et al.
2013/0277574 A1* 10/2013 Dayton ..................... A61L 2/10 250/455.11
2013/0303996 A1 11/2013 Rasooly
2013/0323117 A1 12/2013 Ma et al.
2013/0323119 A1 12/2013 Alwan et al.
2013/0323120 A1* 12/2013 Ma ............................ A61L 2/24 250/455.11
2013/0336839 A1 12/2013 Gil et al.
2014/0038305 A1* 2/2014 Sharavara .............. C09D 11/50 436/164
2014/0131595 A1 5/2014 Nathan et al.
2014/0305470 A1 10/2014 Desu-Kalyanam
2015/0090903 A1 4/2015 Cole
2015/0139858 A1 5/2015 Pedrazzi
2015/0231287 A1 8/2015 Lin et al.
2015/0290347 A1 10/2015 Braden et al.
2015/0327963 A1 11/2015 Fregoso et al.
2016/0324997 A1 11/2016 Dayton
2017/0056539 A1 3/2017 Mellbin
2017/0100495 A1 4/2017 Shur et al.
2017/0136136 A1 5/2017 Li et al.
2017/0165386 A1 6/2017 Huang
2017/0232123 A1* 8/2017 Burapachaisri ....... A61M 39/10 422/24
2018/0055960 A1 3/2018 Reiber et al.
2018/0117191 A1 5/2018 Shell
2018/0117200 A1 5/2018 Stratman et al.
2018/0169286 A1 6/2018 Henniges et al.
2018/0290900 A1 10/2018 Lu et al.
2018/0296709 A1 10/2018 Mishkin et al.
2018/0361001 A1 12/2018 Liao et al.
2019/0328915 A1 10/2019 Paul et al.
2019/0381202 A1 12/2019 Pedrazzi
2020/0188543 A1 6/2020 Etter et al.
2020/0254121 A1 8/2020 Swaney et al.
2021/0036266 A1 2/2021 Kishimoto et al.
2021/0113725 A1 4/2021 Etter et al.
2022/0032081 A1 2/2022 Morio et al.
2024/0058487 A1 2/2024 Swaney et al.

FOREIGN PATENT DOCUMENTS

CN 104815823 A 8/2015
CN 108030940 A 5/2018
JP 2011016074 A 1/2011
JP 2018020091 A 2/2018
KR 100572335 B1 4/2006
RO 120758 B1 7/2006
RU 111976 U1 1/2012
TW 201827112 A 8/2018
WO 9426432 A1 11/1994
WO 2014/021921 A2 2/2014
WO 2014/202401 A1 12/2014
WO 2015/157662 A1 10/2015
WO 2017/062260 A2 4/2017
WO 2019/084029 A1 5/2019
WO 2020/167843 A1 8/2020
WO 2020/167847 A1 8/2020
WO 2020/167850 A1 8/2020

OTHER PUBLICATIONS

Extended European Search Report, dated Jun. 14, 2021, for European Application No. 18870694.9.
Solid-State Lighting, 2013, pp. 1-24, URL:https://microem.ru/files/2014/03/16.10.2013.pdf (XP055697168) [Translation not readily available].
International Search Report and Written Opinion mailed Apr. 29, 2020 for International Application Serial No. PCT/US20/017763 filed on Feb. 11, 2020.
Inolux, IN-C39ATK/IN-C39BTK/ IN-C39CTK UVC Series 3939 UVC LED, <URL:https://www.mouser.jp/datasheet/2/180/IN-C39(X)TK_UVC_Series_V1 .1-1625669.pdf> (Oct. 31, 2018).
Foxx Life Sciences, Autofil Sterile Disposable Vacuum Bottle Top Filters with 0.2um Sterilizing PES Membrane, 500mL, 24/CS, <URL:https://www.amazon.com/Autofil-Sterile-Disposable-Sterilizing-Membrane/dp/BOOHSDSRHA#feature-bullets-btf> (Mar. 14, 2017).
International Search Report and Written Opinion mailed Apr. 23, 2020 for International Application Serial No. PCT/US2020/017767 filed on Feb. 11, 2020.
International Search Report mailed Jun. 15, 2020 for International Application Serial No. PCT/US2020/017771 filed on Feb. 11, 2020.
U.S. Appl. No. 17/429,910, filed Aug. 10, 2021.
U.S. Appl. No. 17/429,916, filed Aug. 10, 2021.
Extended European Search Report, dated Oct. 23, 2023, for European Application No. 20756238.0.
Extended European Search Report, dated Aug. 11, 2023, for European Application No. 20755880.0.
Extended European Search Report, dated Jul. 20, 2023, for European Application No. 20756001.2.

* cited by examiner 102
104
106

STERILIZATION DEVICE

CROSS REFERENCE TO RELATED APPLICATIONS

This application is a continuation of U.S. patent application Ser. No. 16/168,730, filed Oct. 23, 2018, which claims the benefit of U.S. Provisional Patent Application Ser. No. 62/575,899, filed Oct. 23, 2017, the entire disclosures each of which are incorporated herein by reference.

FIELD

The present invention relates generally to sterilization devices.

SUMMARY

Described herein generally are sterilization devices that can allow a physician, advanced practice nurse, registered nurse, nurse, assistant, caregiver, provider, or the like to disinfect surfaces of luminal connection ports during normal and routine connection changing. In some embodiments, the luminal connection ports are on intravenous (IV) lines, IV bags, syringes, and the like. Also, described herein are the methods for using the sterilization devices.

The described sterilization devices can include a body and an adapter cap. In some embodiments, the body can include an activation or on/off switch, at least one indicator light, at least one battery, and a light source. In other embodiments, the body can optionally include a printed circuit board including a processor and memory.

In yet other embodiments, the devices described herein can have independent drivers that do not require a processor. In some embodiments, the independent drivers are LED drivers. In some embodiments, the adapter cap can be sterile.

In some embodiments, the adapter cap can be biocompatible. In other embodiments the adapter cap can be disposable. In some embodiments the adapter cap can be a male luer lock. In other embodiments, the adapter cap can be a female luer lock. The luer lock can be a spinning luer lock that freely spins independently of the body. In other embodiments, the luer lock can also be a fixed luer lock that does not spin.

In some embodiments, the devices can be small, lightweight, and/or handheld. However, the devices need not be small, lightweight, and/or handheld and can include a body that is virtually any size or weight.

In some embodiments, the devices can deliver ultraviolet light to sterilize a luminal connection port. In some embodiments, the ultraviolet light can be ultraviolet C (UVC) light. In other embodiments, the ultraviolet light can be ultraviolet B light.

In one embodiment, the devices can deliver UVC light from a 3.5 mm×3.5 mm light-emitting diode (LED) with a 275 nm wavelength fora 5-10 second interval.

The devices described can effectively denature any microbe or cellular structure on any surface of a luminal connection port.

In some embodiments, the devices can sterilize the luminal connection port within or in less than about 5 seconds. In other embodiments, the devices can sterilize the luminal connection port within or in less than about 10 seconds.

In some embodiments, the optical power from the LED can be about 10 mW. In other embodiments, the optical power from the LED can be up to 50 mW.

In other embodiments, the device can use only about 6 volts of power.

In other embodiments, the devices can have a switch that activates the device to start sterilizing. In some embodiments, the devices can have an auto mode wherein the device begins to sterilize as soon as a connection is completed. In some embodiments, the device can have a multisensor. In other embodiments, the device can have at least one or more sensors.

In other embodiments, the device can have one or more indicator light(s) that can turn green once sterilization is complete. In some embodiments, the device can have one or more indicator light(s) which are blue and turn green once sterilization is complete. In other embodiments, the indicator light(s) can be, but are not limited to, red, blue, purple, yellow, no color, or orange, which then turn green upon completion of sterilization. In some embodiments, there can be a chromatic scheme. In other embodiments, the indicator light(s) are part of the adapter cap.

In other embodiments, the device can have a tactile response to indicate sterilization is complete. In some embodiments, the tactile response is vibration.

In some embodiments, the devices can sterilize the intended surface at a distance of about 1 mm to about 10 mm from the intended surface. In some embodiments, the distance is less than about 10 mm. In other embodiments, the distance is greater than about 1 mm.

Methods are also described for using the herein described devices. Methods can include connecting the devices to luminal connection ports to sterilize the surfaces of the ports within about 5 seconds.

In other embodiments, the methods can include connecting the devices to several luminal connection ports and sterilizing them sequentially one at a time or at the same time. Such sterilization for 1 to 20 ports can take about 30 to about 40 seconds. In other embodiments, methods can include sterilization of 1 to 50 ports.

In other embodiments, the devices described herein can include an inter-locking circuit. In some embodiments, the inter-locking circuit can be connected to the adaptor cap or to a luer to turn on the safety feature. In other embodiments, the inter-locking circuit can have an RFID chip or optical senor configured to allow the adaptor cap and device to communicate. In some embodiments, the adaptor cap and device can communicate via physical, mechanical, or optical communication.

BRIEF DESCRIPTION OF THE DRAWINGS

FIG. 6A. shows the controls (untreated surfaces) with bacterial growth after 48 hours of incubation. FIG. 6B. shows a 99.99% kill after 1 second of UV light exposure.

FIG. 6C. shows a 99.996% kill after 3 seconds of UV light exposure. FIG. 6D. shows a >99.99999% kill after 7 seconds of UV light exposure.

DETAILED DESCRIPTION

Figures 1, 2:
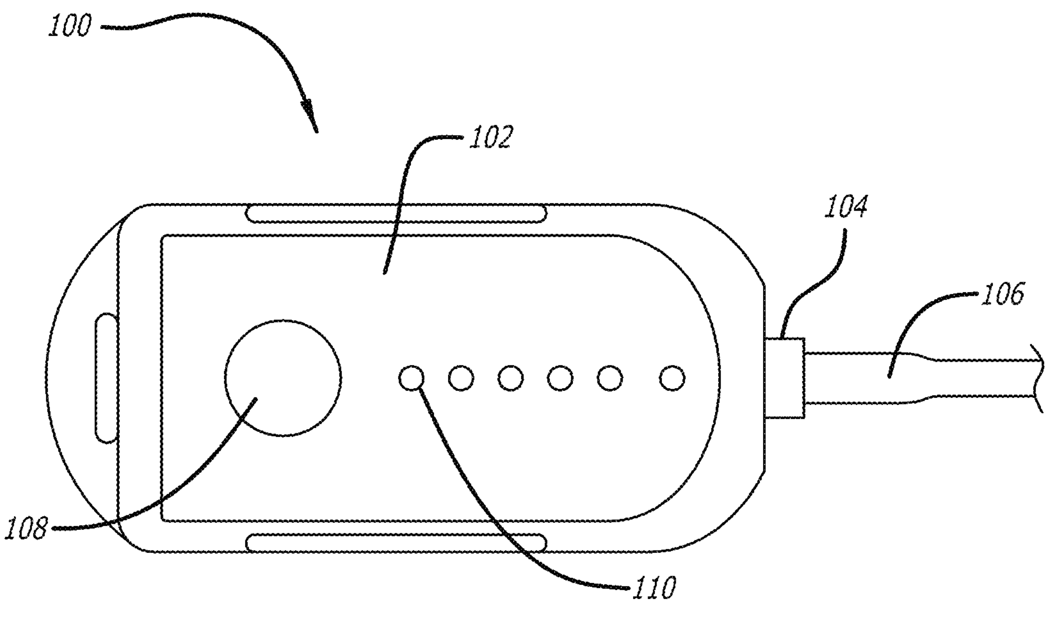
FIG. 1 illustrates an example embodiment of a device as described herein.
FIG. 2 illustrates a top end view of an example embodiment of a device as described herein.

Described herein generally are devices that can reduce, eliminate, and/or prevent chances of infection.

In some embodiments, the devices are sterilization devices utilized for sterilization of the surfaces of luminal connection ports. Luminal connection ports can include, but are not limited to IV line connection ports, IV bag connections, syringes, peripherally inserted central catheter lines, catheter connections, microcatheter connections, feeding tub connections, infusion pump connections, chest tub connections, intubation lines connections, colostomy bag connections, and the like.

Sterilization of the surfaces of these types of connection ports can be very time consuming. In some instances, a patient may require 1 to 20 IV line connection port changes per day along with port changes every three to four days. Sterilization using the described devices can reduce this time burden, in some cases by about 66%.

Catheter and IV related bloodstream infections are common, and are primarily caused by microbial ingress, whether via airborne route or gross contact contamination, through a surface entry of the IV connector or via an access point around the venous catheter insertion. As previously described, the Center for Disease and Control (CDC) and Joint Commission recommend scrubbing a port for at least 15 seconds with an isopropyl pad in order to properly sterilize that port. This very time consuming and tedious sterilization process is thought to disinfect the surface of a port allowing the safe administration of fluids.

Patients in care settings typically require 1 to 20 IV connector engagements per day along with connector changes every three to four days. Additionally due to time constrains, staff changes, and nursing irregularities, proper IV connector care is a consistent problem and contributing factor to healthcare acquired infections (HAI) known as CRBSI/CLBSI, catheter-related/central line bloodstream infections. Thus, there is a need in the field for an efficient time saving device to disinfect surfaces of IV connectors.

Microbial ingress is an ongoing problem with luminal connection ports. Companies have provided methods for disinfecting ports. However, these devices require longer disinfecting times, e.g., greater than 1 min, cost more than the present devices, and have inconsistent disinfecting results.

The present devices can sterilize luminal connection ports quicker and more efficiently than even the present standards outline. The present devices can provide clinical benefits that enhance provider efficiency, and improve clinical outcomes while delivering significant cost savings. In some embodiments, the present devices can be built on a device/disposable platform that can deliver complete sterilization and at least a 4-log (99.99%) microbial reduction. This 4-log (99.99%) microbial reduction is greater than standard methods which only promise to deliver disinfection. In other embodiments the microbial reduction can be about a 4-log microbial reduction, about a 5-log microbial reduction, about a 6-log microbial reduction, about a 7-log microbial reduction, about a 8-log microbial reduction, at least about a 4-log microbial reduction, at least about a 5-log microbial reduction, at least about a 6-log microbial reduction, at least about a 7-log microbial reduction, at least about a 8-log microbial reduction, more than a 4-log microbial reduction, more than a 5-log microbial reduction, more than a 6-log microbial reduction, more than a 7-log microbial reduction, more than a 8-log microbial reduction, or between about a 4-log microbial reduction to about a 8-log microbial reduction.

The devices described herein can reduce methicillin-resistant *Staphylococcus aureus* (MSRA) bacteria on IV connectors with 99.99% kill after 1 second, 99.999% kill after 3 seconds, and >99.99999% after 7 seconds of UV light exposure. These results demonstrate the effectiveness of the devices described herein. In comparison, current methods on the market take days to reach only a 98% kill, whereas the devices described herein take a second to achieve a 99.99% kill.

In some embodiments, the devices described herein can be used to sterilize port surfaces of luminal devices which are either connected to a delivery bag (e.g., IV bag) or directly to a patient. A patient as used herein can be a mammal such as a humans, horses, camels, dogs, cats, cows, bears, rodents, oxen, bison, buffalo, caribou, moose, deer, elk, sheep, goats, pigs, rabbits, pouched mammals, primates, carnivores, and the like. When used with/for patients, the devices can meet the highest safety standards imposed by local, regional, or governmental regulations for sterilization protocols.

The Center for Disease Control and Joint Commission sterilization protocols include scrubbing an IV connector engagements/surfaces with an isopropyl pad for 15 seconds. The devices described herein can reduce sterilization time when compared to the times set by the CDC and the Joint Commission. The present devices can sterilize a luminal connection ports in less than about 10 seconds or less than about 5 seconds. Thus, the present devices can save time when sterilizing.

Figure 3:
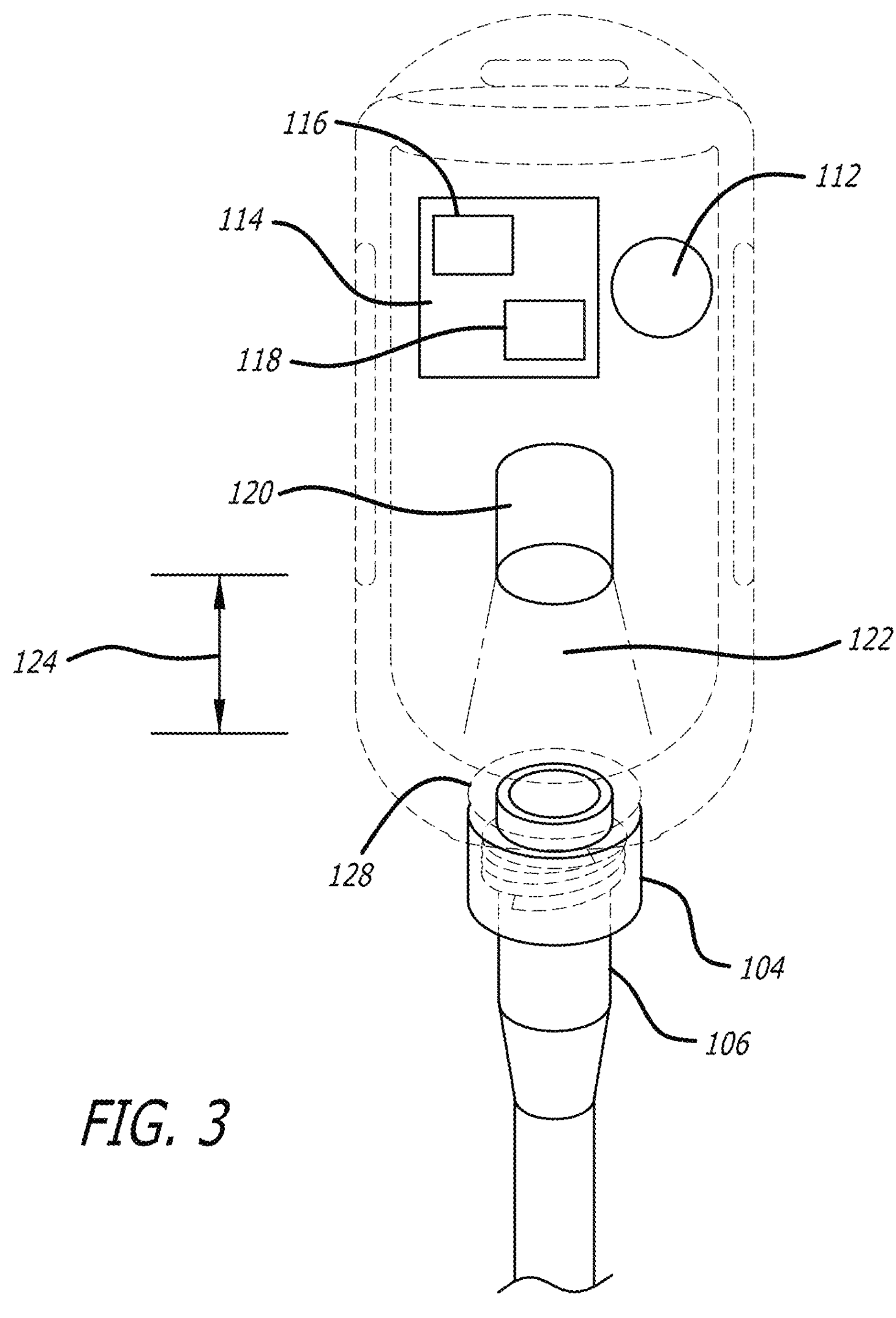
FIG. 3 illustrates an embodiment on the internal LED sterilizing an intended luminal connection port.

One embodiment of a device as described herein, device 100, is illustrated in FIGS. 1-3. Device 100 can include body 102.

Body 102 can be formed of non-conductive materials such as polymers. Exemplary polymers include, but are not limited to polyurethanes, silicones, polyesters such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; carboxymethyl cellulose; synthetic and natural rubbers such as polysiloxanes, latex, polymerized isoprene, bromo isobutylene isoprene, chloro isobutylene isoprene, polychloroprene, chlorosulphonated polyethylene, ethylene propylene, ethylene propylene diene monomer, fluoro silicone, hydrogenated nitrile butadiene, polyisoprene, isobutylene isoprene butyl, methyl vinyl silicone, acrylonitrile butadiene, acrylonitrile butadiene carboxy monomer, styrene butadiene, epichlorodydrin; and combinations thereof.

In some embodiments, body 102 can be formed of cyclic olefin copolymers. In other embodiments, body 102 can be formed of TOPAS®. TOPAS can be used to allow for at least 80% of the UV light to penetrate through it. Many other plastics/polymers will not allow for at least 80% of the UV light to penetrate through it.

The polymer or combination of polymers chosen to form body 102 can be rigid enough to hold a particular configuration and perform its intended function. In some embodiments, the polymer used is a thermal set rigid plastic. In other embodiments, the polymer is a flexible nylon or rubber polymer.

Body 102 can include or be connected to adapter cap 104. Adapter cap 104 can be virtually any type of connector that weds with a luminal connection port. In one embodiment, catheter line 106 is connected to adapter cap 104.

In some embodiments, adapter cap 104 can be sterile. In other embodiments, adapter cap 104 can be biocompatible. In some embodiments, adapter cap 104 can be disposable. Adapter cap can be any kind of cap connector including, but not limited to, a male leur lock, a female luer lock, a Y connector or the like, or a combination thereof. In some embodiments the adapter cap can be a male luer lock. In other embodiments, the adapter cap can be a female luer lock. The luer lock can be a spinning luer lock that freely spins independently of the body. In other embodiments, the luer lock can also be a fixed luer lock that does not spin. In some embodiments, adapter cap 104 can have tabs 130 on one end which can connect to body 102 by friction fitting. In other embodiments, adapter cap 104 can magnetically fit with body 102.

In some embodiments, adapter cap 104 can be threaded to accept a threaded luminal connection port. In other embodiments, adapter cap 104 may not be threaded so that it can be friction fitted to a luminal connection port. In some embodiments, adapter cap 104 can magnetically fit with the luminal connection port. In other embodiments, the device can include a circular recess so that any type of adapter cap can fit in it.

In some embodiments, adapter cap 104 can include a silica lens to allow ultraviolet light to penetrate and sterilize luminal connection port(s).

Body 102 can include activation or on/off switch 108. Switch 108 can be a push button, a press button, or a toggle button/switch.

In other embodiments, body 102 may not include a switch. In such an embodiment, body 102 can include an auto mode wherein the device begins to sterilize as soon as a connection is completed. In some embodiments, the device can have at least one or more sensors. In other embodiments, the device can have multi-sensors. In some embodiments, the at least one or more sensors can be located anywhere on the device. In other embodiments, the multi-sensors can be located anywhere on the device. In some embodiments, the at least one or more sensors are configured to allow the device to begin sterilization upon the connection between the device and a luminal connection port. In other embodiments, the multi-sensors are configured to allow the device to begin sterilization upon the connection between the device and a luminal connection port.

A device can include at least one indicator light. Body 102 includes six indicator lights 110. Indicator light(s) can be one color prior to inserting adapter cap 104 into an IV connection port. In other embodiments, indicator light(s) 106 can turn red after adapter cap 102 is inserted into a luminal connection port when the light(s) can change color indicating a sufficient connection. In some embodiments, when a luminal connection port has been properly sterilized the indicator light(s) can change color. The indicator light(s) signal to a user that the port is sterilized and the device can be removed. In some embodiments, once the device is removed, the indicator lights can turn off. In other embodiments, switch 108 is pushed to power off the device.

Indicator lights 110 on body 102 can progressively illuminate, for example the light adjacent to switch 108 to the light adjacent to adapter cap 104. This progression can display the sterilization process time.

As described, different light color combinations can be used to indicate device status. In some embodiments, red light can indicate a port that is not sterilized and green light can indicate proper sterilization. In some embodiments, a blue light can be used to indicate in process. In some embodiments, only a single light is needed to provide status. In other embodiments, multiple lights can be used to provide status.

In some embodiments, there can be a chromatic scheme. In other embodiments, indicator lights 110 can be part of adapter cap 104. In other embodiments, indicator lights can be located anywhere on the device. In some embodiments, the chromatic scheme can be used to determine the status of the sterilization. In other embodiments, the chromatic scheme can include blue light(s) which indicate the device has not yet been sterilized. In some embodiments, the chromatic scheme can include green light(s) which indicate the device has been sterilized. In other embodiments, the chromatic scheme can include red light(s) or orange light(s) which indicate the device has not been sterilized. In some embodiments, the chromatic scheme can include blue light(s) which indicate that the device has been sterilized.

In some embodiments, there is a substrate or liquid situated in a base of the adapter cap which can change colors at specific wavelengths. In other embodiments, the substrate or liquid can be clear and turn green upon completion of sterilization. In some embodiments, when the cap is exposed to UV light the substrate will change. Once the substrate changes color it can be irreversible so that the cap is single use and cannot be used again.

Body 102 can house at least one battery. Body 102 can optionally include a printed circuit board including at least one processor and memory. Battery 112 can be any standard sized battery. Standard size batteries can include, but are not limited to round, cylindrical batteries such as AA, AAA, AAAA, C, D, and button cell (such as lithium button), coin cell, and non-round batteries such as box batteries, and the like. In still other embodiments, proprietary battery packs can be provided to fit a particular slot or opening on or in a device. In some embodiments, the device uses a battery providing about 4 volts of power, about 5 volts of power, about 6 volts of power, about 7 volts of power, about 8 volts of power, about 9 volts of power, about 10 volts of power, about 11 volts of power, about 12 volts of power, at least about 4 volts of power, at least about 5 volts of power, at least about 6 volts of power, at least about 7 volts of power, at least about 8 volts of power, at least about 9 volts of power, at least about 10 volts of power, at least about 11 volts of power, at least about 12 volts of power, more than about 4 volts of power, more than about 5 volts of power, more than about 6 volts of power, more than about 7 volts of power, more than about 8 volts of power, more than about 9 volts of power, more than about 10 volts of power, more than about 11 volts of power, more than about 12 volts of power, between about 4 volts of power to about 11 volts of power, or between about 4 volts of power to about 12 volts of power.

In some embodiments, two voltages are provided. Either voltage can be about 9 volts of power, about 9.5 volts of power, about 10 volts of power, about 10.5 volts of power, about 11 volts of power, about 11.5 volts of power, about 12 volts of power, about 12.5 volts of power, about 13 volts of power, about 13.5 volts of power, about 14 volts of power, about 14.5 volts of power, between about 9 volts of power and about 13.5 volts of power, between about 9 volts of power to about 13 volts of power, between about 9 volts of power to about 12 volts of power, or between about 9 volts of power to about 11 volts of power. In other embodiments, a battery can provide two voltages of power, one of about 9 volts of power to about 13.5 volts of power, and another of about 9 volts to about 12 volts.

Battery life can be about 6 months to 1 year. In some embodiments, the life of the battery can be about 28 days, about 30 days, about 1 month, about 2 months, about 3 months, about 4 months, about 5 months, about 6 months, about 7 months, about 8 months, about 9 months, about 10 months, about 11 months, about 1 year, at least about 1 day, at least about 1 week, at least about 1 month, at least about 6 months, or at least about 1 year.

In some embodiments, the devices can be used once and then discarded; in other words, the devices can be disposable. In other embodiments, the devices can be reusable allowing a single device to sterilize at least about 10, at least about 50, at least about 100, at least about 250, at least about 500, or at least about 1,000 ports using a single battery. In some embodiments, devices can be discarded after battery depletion. In other embodiments, a battery can be replaced and the device can be used again. In still other embodiments, the battery can be re-charged and the device used again and again. This great number of disinfections using a single device can save cost because one device can sterilize numerous ports instead of using several hundreds disposable isopropyl pads a day.

The devices can be washable and sterilizable using conventional sterilization techniques. In some embodiments, the devices are sealed sufficiently to allow multiple washings with a detergent or alcohol based cleaner without damaging the device. Further, the devices can be sterilized using gamma irradiation techniques.

In some embodiments, the devices can automatically shut off when the battery is below the threshold to produce enough energy to sterilize the intended surface. This automatic shut off can prevent a device from not completing a sterilization.

In some embodiments, battery 112 can be removed as needed to clean and/or sterilize the device. In other embodiments, battery 112 can be removed to be replaced. In some embodiments, battery 112 lasts for the life of the product without replacement.

Optional printed circuit board 114 can include processor 116 that can execute instructions stored in memory 118. Instructions can include sterilization times, light intensities, indicator light scenarios, sensor inputs/outputs, and the like.

In other embodiments, the devices described herein can have independent drivers that do not require a processor. In some embodiments, the independent drivers are LED drivers. The LED drivers can use transistors which do not include using a microprocessor.

In some embodiments, body 102 includes a light source 120. The light source can be an incandescent bulb, a halogen bulb, a xenon bulb, a laser, a monochromatic light, or a light emitting diode (LED). In other embodiments, the light source can be anything that will emit ultraviolet light, ultraviolet C light, or a combination thereof.

In some embodiments, light source 120 can deliver or project light 122 to sterilize a luminal connection port at adapter port 104. In some embodiments, the light is ultraviolet light. In some embodiments, the light is ultraviolet C (UVC) light. The light can be delivered from about a 3.5 mm×3.5 mm LED. In other embodiments, the LED can be about 0.5 mm×0.5 mm, about 0.5 mm×1.0 mm, about 1.0 mm×1.0 mm, about 1.5 mm×2.5 mm, about 2.0 mm×2.0 mm, about 2.5 mm×3.5 mm, about 3.0 mm×3.0 mm, about 3.5 mm×4.5 mm, about 4.0 mm×4.0 mm, about 4.5 mm×5.5 mm, or about 5.0 mm×5.0 mm.

In some embodiments, the LED driver can operate at a constant current over the device as the battery degrades. In some embodiments, the LED driver can operate at a constant power over the device as the battery degrades.

In other, embodiments there can be LED modulation. LED modulation can be at least about 10 Hz, at least about 50 Hz, at least about 100 Hz, at least about 500 Hz, at least about 1 kHz, at least about 10 kHz, at least about 100 kHz, at least about 500 kHz, at least about 1 MHz, at least about 10 MHz, at least about 100 MHz, at least about 500 MHz, at least about 1 GHz, at least about 10 GHz, at least about 100 GHz, between about 10 Hz and about 500 GHz, between about 1 MHz and about 500 GHz, between about 1 MHz and about 1 GHz, between about 1 kHz and about 500 GHz, between about 1 Hz and about 500 MHz, between about 1 Hz and about 1 kHz, between about 1 kHz and about 1 MHz, between about 1 Hz and about 500 kHz, between about 500 kHz and about 500 MHz, any combination of a end value thereof. In one embodiment, the modulation can be between about 10 Hz and about 10 GHz. In some embodiments, there is no LED modulation but rather the devices described herein can operate using constant current mode. In other embodiments, whether the device is using constant power, constant current, or LED modulation, it can be dependent on the life of the battery. In some embodiments, the LED drivers can operate at constant current, constant power, and/or LED modulation.

In some embodiments, UVC light can be delivered with a wavelength of about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225, nm, about 230 nm, about 235 nm, about 240 nm, about 245 nm, about 250 nm, about 255 nm, about 260 nm, about 265 nm, about 270 nm, about 275 nm, about 280 nm, between about 100 nm to about 160 nm, between about 160 nm to about 210 nm, between about 210 nm to about 260 nm, or between about 220 nm to about 280 nm. In some embodiments, UVC light can be delivered with a wavelength of about 275 nm.

The higher the wavelength utilized, the less energy that is expelled allowing for the devices to be more efficient.

In other embodiments, UVB light can be delivered with a wavelength of about 280 nm, about 285 nm, about 290 nm, about 295 nm, about 300 nm, about 305 nm, about 310 nm, about 315 nm, between about 280 nm to about 300 nm, or between about 285 nm to about 315 nm.

In some embodiments, UV light, B or C, can be delivered for less than about a 5 sec or less than about 10 sec. In some embodiments, light is delivered for between about 5 sec and about 10 sec. In other embodiments, UV light, B or C, can be delivered within about 1 sec, about 2 sec, about 3 sec, about 4 sec, about 5 sec, about 6 sec, about 7 sec, about 8 sec, about 9 sec, about 10 sec, about 11 sec, about 12 sec, about 13 sec, about 14 sec, about 15 sec, about 16 sec, about 17 sec, about 18 sec, about 19 sec, about 20 sec, about 21 sec, about 22 sec, about 23 sec, about 24 sec, about 25 sec, about 26 sec, about 27 sec, about 28 sec, about 29 sec, about 30 sec, about 31 sec, about 31 sec, about 32 sec, about 33 sec, about 34 sec, about 35 sec, about 36 sec, about 37 sec, about 38 sec, about 39 sec, about 40 sec, about 41 sec, about 42 sec, about 43 sec, about 44 sec, about 45 sec, about 46 sec, about 47 sec, about 48 sec, about 49 sec, about 50 sec, about 51 sec, about 52 sec, about 53 sec, about 54 sec, about 55 sec, about 56 sec, about 57 sec, about 58 sec, about 59 sec, about 60 sec, or about one minute.

In some embodiments, UV light, B or C, can be delivered for less than about 1 sec, less than about 2 sec, less than about 3 sec, less than about 4 sec, less than about 5 sec, less than about 6 sec, less than about 7 sec, less than about 8 sec, less than about 9 sec, less than about 10 sec, less than about 11 sec, less than about 12 sec, less than about 13 sec, less than about 14 sec, less than about 15 sec, less than about 16 sec, less than about 17 sec, less than about 18 sec, less than about 19 sec, less than about 20 sec, less than about 21 sec, less than about 22 sec, less than about 23 sec, less than about 24 sec, less than about 25 sec, less than about 26 sec, less than about 27 sec, less than about 28 sec, less than about 29 sec, less than about 30 sec, less than about 31 sec, less than about 32 sec, less than about 33 sec, less than about 34 sec, less than bout 35 sec, less than about 36 sec, less than about 37 sec, less than about 38 sec, less than about 39 sec, less than about 40 sec, less than about 41 sec, less than about 42 sec, less than about 43 sec, less than about 44 sec, less than about 45 sec, less than about 46 sec, less than about 47 sec, less than about 48 sec, less about 49 sec, less than about 50 sec, less than about 51 sec, less than about 52 sec, less than about 53 sec, less than about 54 sec, less than about 55 sec, less than about 56 sec, less than about 57 sec, less than about 58 sec, less than about 59 sec, less than about 60 sec, or less than about one minute.

In some embodiments, UV light, B or C, can be delivered for more than about 1 sec, more than about 2 sec, more than about 3 sec, more than about 4 sec, more than about 5 sec, more than about 6 sec, more than about 7 sec, more than about 8 sec, more than about 9 sec, more than about 10 sec, more than about 11 sec, more than about 12 sec, more than about 13 sec, more than about 14 sec, more than about 15 sec, more than about 16 sec, more than about 17 sec, more than about 18 sec, more than about 19 sec, more than about 20 sec, more than about 21 sec, more than about 22 sec, more than about 23 sec, more than about 24 sec, more than about 25 sec, more than about 26 sec, more than about 27 sec, more than about 28 sec, more than about 29 sec, more than about 30 sec, more than about 31 sec, more than about 32 sec, more than about 33 sec, more than about 34 sec, more than about 35 sec, more than about 36 sec, more than about 37 sec, more than about 38 sec, more than about 39 sec, more than about 40 sec, more than about 41 sec, more than about 42 sec, more than about 43 sec, more than about 44 sec, more than about 45 sec, more than about 46 sec, more than about 47 sec, more than about 48 sec, more than about 49 sec, more than about 50 sec, more than about 51 sec, more than about 52 sec, more than about 53 sec, more than about 54 sec, more than about 55 sec, more than about 56 sec, more than about 57 sec, more than about 58 sec, more than about 59 sec, more than about 60 sec, more than about one minute, between about 0.1 sec to about 5 sec, between about 2 sec to about 3 sec, between about 5 sec to about 7 sec, between about 5 sec to about 10 sec, between about 5 sec to about 11 sec, between about 6 sec to about 12 sec, between about 11 sec to about 15 sec, between about 13 sec to about 25 sec, between about 15 sec to about 30 sec, between about 25 sec to about 35 sec, between about 25 sec to about 45 sec, or between about 25 sec to about 60 sec.

In accordance with signal processing, in some embodiments the pulsed light applied can be a square signal, a rectangular signal, a cosine squared signal, a Dirac signal, a sinc signal, a Gaussian signal, or a combination thereof.

In some embodiments, device 100 can deliver ultraviolet C (UVC) light to sterilize a luminal connection port. In one embodiment, the UVC light can be delivered from a light source having a size of about 3.5 mm×3.5 mm with a wavelength of about 275 nm for an interval of about 5 sec to about 10 sec at an optical power of about 10 mW to about 50 mW. In another embodiment, the UVC light can be delivered from a light source having a size of about 3.5 mm×3.5 mm with a wavelength of about 275 nm for an interval of less than about 5 sec at an optical power of about 10 mW to about 50 mW. In another embodiment, the UVC light can be delivered from a light source having a size of about 3.5 mm×3.5 mm with a wavelength of about 275 nm for an interval of less than about 10 sec at an optical power of about 10 mW to about 50 mW.

The described light delivery can effectively denature any microbe or cellular structure on the surface of the luminal connection port.

In some embodiments the optical power can be about 1 mW, about 2 mW, about 3 mW, about 4 mW, about 5 mW, about 6 mW, about 7 mW, about 8 mW, about 9 mW, about 10 mW, about 11 mW, about 12 mW, about 13 mW, about 14 mW, about 15 mW, about 16 mW, about 17 mW, about 18 mW, about 19 mW, about 20 mw, about 25 mW, about 30 mw, between about 1 mW to about 5 mW, between about 1 mW to about 10 mW, between about 5 mW to about 10 mW, between about 5 mW to about 15 mW, between about 10 mW to about 15 mW, between about 10 mW to about 20 mW, or between about 10 mW to about 30 mW. In some embodiments, the optical power can be about 10 mW. In other embodiments, the optical power can be at least 6 mW.

One or more lens is used in conjunction with light source 120 to focus the light onto adapter port. The lenses can be made of plastics or glass or may be formed of a transparent polymer used to make the housing. The lenses can be made to provide a particular focal length to the light. In some embodiments, curvature of the inner or outer surface of the lens, thickness of the lens, refractive index of the lens and the like can be used to provide a particular focal length. In some embodiments, focal length is generally from the light source to the adapter port. In other embodiments, the one or more lens can be a conical lens. The conical lens can be a lens with a surface that is a cone instead of the usual sphere. In some embodiments, the conical lens can be used to transform collimated light into a ring to create an approximation of a Bessel beam. In some embodiments, the one or more lens can be a conical TOPAS® lens. In other embodiments, the conical lens can reduce the time frame to focus promoting time efficiency.

In some embodiments, light source 120 can be at a focal length or distance 124 from the adapter cap 104. In some embodiments, distance 124 can be about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, less than about 1 mm, less than about 2 mm, less than about 3 mm, less than about 4 mm, less than about 5 mm, less than about 6 mm, less than about 7 mm, less than about 8 mm, less than about 9 mm, less than about 10 mm, less than about 11 mm, less than about 12 mm, less than about 13 mm, less than about 14 mm, less than about 15 mm, less than about 16 mm, less than about 17 mm, less than about 18 mm, less than about 19 mm, less than about 20 mm, more than about 1 mm, more than about 2 mm, more than about 3 mm, more than about 4 mm, more than about 5 mm, more than about 6 mm, more than about 7 mm, more than about 8 mm, more than about 9 mm, a more than bout 10 mm, more than about 11 mm, more than about 12 mm, more than about 13 mm, more than about 14 mm, more than about 15 mm, more than about 16 mm, more than about 17 mm, more than about 18 mm, more than about 19 mm, more than about 20 mm, between about 1 mm about 5 mm, between about 5 mm and about 10 mm, between about 7 mm and about 10 mm, between about 5 mm and about 15 mm, between about 8 mm and about 15 mm, or between about 14 mm and about 20 mm. Distance 124 can be between about 5 mm to about 10 mm from the intended surface.

In some embodiments, the light output homogeneity can be characterized such that all areas of the intended surface to be sterilized receive enough exposure. In other embodiments, the least amount of light output can result in an acceptable amount of radiation to sterilize the intended surface. The optical power of the light output homogeneity can be about 6 mW, about 7 mW, about 8 mW, about 9 mW, about 10 mW, at least about 6 mW, at least about 7 mW, at least about 8 mW, at least about 9 mW, at least about 10 mW, more than about 6 mW, more than about 7 mW, more about 8 mW, more than about 9 mW, more than about 10 mW, less than about 6 mW, less than about 7 mW, less than about 8 mW, less than about 9 mW, less than about 10 mW, between about 6 mW to about 10 mW, between about 7 mW to about 9 mW, between about 7 mW to about 8 mW, or about 8 mW to about 9 mW.

In some embodiments, the devices are handheld. In some embodiments, the devices are ergonomic. The devices can be disposable and used for a single use. In other embodiments, the devices can be used multiple times.

In some embodiments, a port cap can be provided to connect to a luminal connection port to keep it sterile until it is hooked and/or used.

In other embodiments, the devices described herein can include an inter-locking circuit. The inter-locking circuit can be a safety feature which can prevent the UV light from being emitted prematurely. In some embodiments, the inter-locking circuit can be an inter-locking circuit cap which is connected to the device. When the inter-locking circuit cap is connected to the device, the safety aspect prevents the UV light from being emitted prematurely.

In other embodiments, the inter-locking circuit can be connected to the adaptor cap or to a luer to turn on the safety feature. In other embodiments, the inter-locking circuit can have an RFID chip or an optical senor configured to allow the inter-locking circuit cap and device to communicate. In some embodiments, the inter-locking safety feature can be triggered when the inter-locking circuit cap can be connected to the device and the inter-locking circuit cap and RFID/optical sensor can communicate. In some embodiments, the adaptor cap and device can communicate via physical, mechanical, or optical communication.

Using the present devices during surgery can save time and provide a better working environment. It is not uncommon for a surgeon to be wearing several layers of clothing along with surgical barriers, including gloves, face barriers, goggles, hats, and overcoats, to name a few, during a given surgical procedure, contributing to discomfort and fatigue normally associated with hot and bright surgical working environments. The devices described herein provide specific advantages for patient and physician comfort as well as to a surgeon's stamina by decreasing the time of a procedure and/or the time a patient is under anesthesia.

Compounding matters, the complexity of contemporary operating rooms has increased over the years as a result of the extra equipment, fixtures, associated power cords and the like required for ever more complicated surgeries. Such situations are not conducive to comfortable, non-fatiguing surgical environments. The ease of use of the presently described devices and can address and assist in overcoming these issues.

Patient comfort during a surgical procedure is very important, especially when the patient is under local anesthesia and is conscious. It is not uncommon for bright lights to be focused on at least a portion of a patient, typically on the target surgical site. Such lighting systems can get hot and make a patient uncomfortable. Patients who are uncomfortable commonly are more on edge, squirm and/or twitch, or are tense. These are not ideal situations for a patient undergoing surgery. The present lighting device's ability to adequately illuminate a surgical site without the need to direct high intensity lighting during use can simplify and shorten a medical procedure, provide enhanced patient comfort and compliance, and improve the medical procedure's outcome; all while providing the surgeon with enhanced visual control of the process.

Figure 4:
FIG. 4 illustrates an example embodiment of a device as described herein being used to sterilize a connection port.
Figure 5:
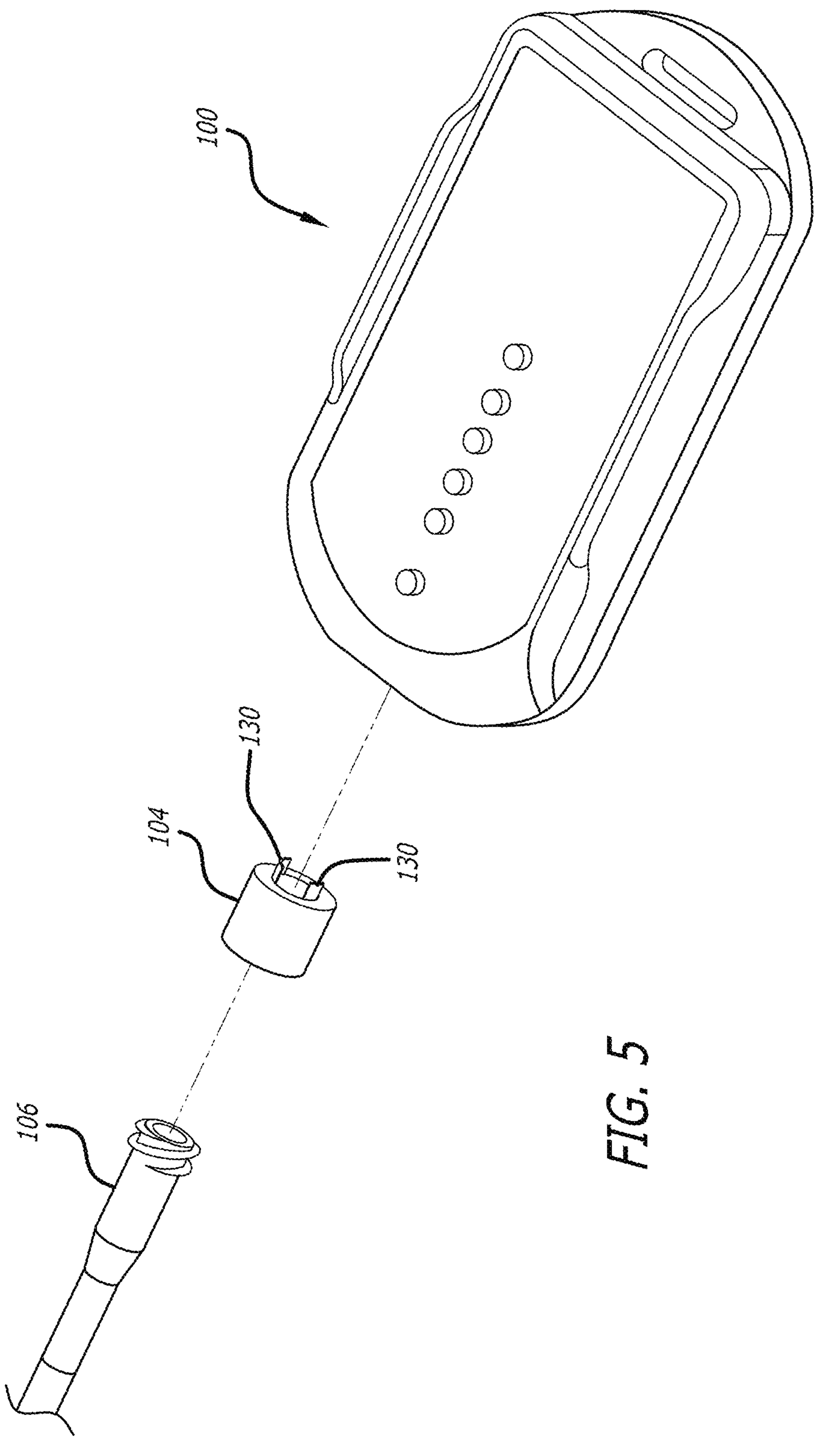
FIG. 5 illustrates an exploded view of an example embodiment of a device as described herein being used to sterilize a connection port.
Figure 6A:
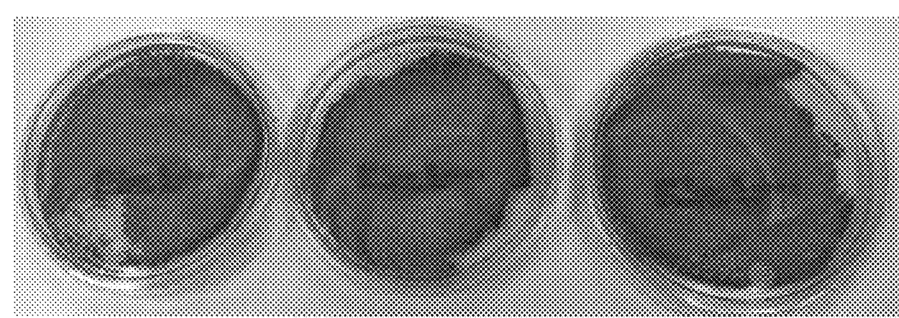
FIGS. 6A-6D illustrate the experimental results for Example 1.
Figure 6B:
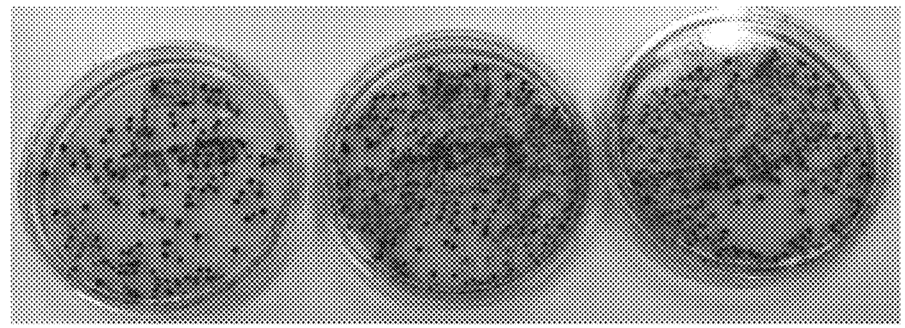
Figure 6C:
Figure 6D:
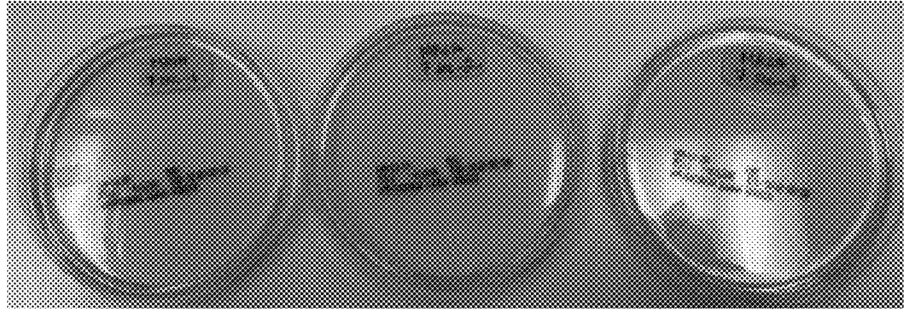

Methods are also described for using the herein described devices. An embodiment illustrating use of a device is in FIG. 4. A user attaches adapter cap 104 to luminal connection port (not illustrated) on IV line 126. Adapter port 104 is screwed into device 100 at port 128. The user starts device 100 by activating switch 108. A light indicates that the device is sterilizing the luminal connection port and then changes color when the port is sterilized.

In another embodiment, a user attaches adapter cap 104 to luminal connection port (not illustrated) on IV line 126. Adapter port 104 is screwed into device 100 at port 128 and the device automatically activates and begins to sterilize the luminal connection port. A light indicates when the port is sterilized. In either method, the sterilized port can then be connected as desired.

In some embodiments, the methods can include connecting the devices to several luminal connection ports and sterilizing them sequentially one at a time. Such a mass sterilization for 6-8 ports can take about 30 to about 40 seconds.

In other embodiments, a device can include multiple sterilization ports to connect multiple luminal connection ports at one time. Then, when all the ports are connected, the device can sterilize them all at one time.

In some embodiments, the device can be prepackaged so there is no gap in exposure time. For example, the device and adaptor cap can be prepackaged for a single use. In other embodiments, the device can be prepackaged and the adapter caps can be separately packaged. The adaptor caps can be disposable and for a single use.

In some embodiments, kits including the herein described devices can be provided. In one embodiment, a kit can include a device such as device 100 in an appropriate packaging and instructions for use.

In one embodiment, a kit can include a disposable device such as device 100 in an appropriate packaging and instructions for use.

In one embodiment, a kit can include a device such as device 100 in an appropriate packaging, a recharging cradle, and instructions for use.

Example 1

The devices as described herein, were used to test the efficacy of killing methicillin-resistant *Staphylococcus aureus* (MRSA) on IV connector surfaces after 1 second, after 3 seconds, and after 7 seconds of exposure time.

Culture Preparation

MRSA was plated onto tryptic soy agar supplemented with 5% sheep blood (TSAB) and incubated at 35° C. for 24 hours. Well isolated colonies were transferred into phosphate buffer water (PBW) and adjusted to approximately 1×108 CFU/mL before the testing was conducted. The inoculum was used to contaminate the septum surfaces of IV connectors.

Quantitative Testing

Each test surface was inoculated with 50 μL of the inoculum and left to air dry for 4 hours at ambient temperature inside a biological safety cabinet. Inoculated test surfaces were individually placed into UV devices and subjected to one second, three seconds, and seven seconds of exposure to the UV light. Three untreated test surfaces were used as controls to determine starting population size of the inoculum. All tests were performed in triplicate. Remaining bacteria were recovered from the test surfaces by washing the surfaces 8 times using neutralizing solution and PBW and plated onto HardyCHROM *Staph aureus* agar.

Untreated-controls of bacterial cultures were serially diluted and plated using AC Petrifilm and incubated at 35° C. for 48 hrs. Colonies were counted following incubation and used to calculate percent reduction (efficacy) of UV light against the test bacteria.

TABLE 1

MRSA colony forming units (CFU) on test surfaces with and without UV exposure in the UV device.

| UV Exposure | Test Avg. CFU/Test Surface (average of 3 tests) | Log | Log Reduction | % Reduction |
|---|---|---|---|---|
| Control (untreated) | 8,233,333 | 6.916 | | |
| 1 sec UV | 300 | 2.478 | 4.44 | 99.996 |
| 3 sec UV | 30 | 1.472 | 5.44 | 99.996 |
| 7 sec UV | <1 | 0.000 | 6.92 | >99.99999 |

CFU: Conly Forming Unites, Detection Limit = 1 CFU; % Reduction-Percent difference between untreated population The devices described herein can reduce MSRA bacteria on IV connectors with 99.99% kill after 1 second, 99.999% kill after 3 seconds, and >99.99999% after 7 seconds of UV treatment. These results demonstrate the effectiveness of the devices described herein. In comparison, current methods on the market take days to reach only a 98% kill, whereas the devices described herein take a second to achieve a 99.99% kill.

FIG. 6 illustrates the experimental results for Example 1. FIG. 6A. shows the controls (untreated surfaces) with bacterial growth after 48 hours of incubation. FIG. 6B. shows the 99.99% kill after 1 second of UV light exposure (where the bacterial growth was after 48 hours of incubation). FIG. 6C. shows the 99.996% kill after 3 seconds of UV light exposure (where the bacterial growth was after 48 hours of incubation). FIG. 6D. shows the >99.99999% kill after 7 seconds of UV light exposure (where the bacterial growth was after 48 hours of incubation).

Example 2

Sterilization of IV Connection Ports

Post surgery a patient is in a recovery room and is connected to three IV bags. The IV bags need to be changed. A medical professional comes in and removes the bags. Prior to attaching new bags, the medical professional uses the devices described herein to sterilize the surface of the connection ports. The medical professional inserts the device into one/the first connection port and switches on the device. The LED indicator lights start illuminating red incrementally. After about five seconds the red LED indicator lights turn green. The green LED indicator lights signal to the medical professional that surface of the connection port is sterilized. The medical professional then attaches the new bag. Then using the same procedure the medical professional sterilizes the remaining two connection ports and attaches the new bags. The IV bag change is then complete.

Example 3

Sterilization of IV Connection Ports 2

Post surgery a patient is in a recovery room and is connected to three IV bags. The IV bags need to be changed. A medical professional comes in and removes the bags. Prior to attaching new bags, the medical professional uses the devices described herein to sterilize the surface of the connection ports. The medical professional inserts the device into one/the first connection port and switches on the device. The LED indicator lights start illuminating red incrementally. After about five seconds the red LED indicator lights turn off, and the LED indicator lights turn green. The green LED indicator lights signal to the medical professional that surface of the connection port is sterilized. The medical professional attaches a sterile port cap to the connection port to keep it sterile while she sterilizes the remaining connection ports. After the sterilization of each connection port she connects a sterile port cap to the connection port. Once the medical professional has completed sterilizing all the connection ports she begins hooking up the new bags. She first removes one port cap and hooks up the new bag. This is repeated until are three bags are up. The IV bag change is then complete.

Example 4

Post surgery a patient is in a recovery room and is connected to three IV bags. The IV bags need to be changed. A medical professional comes in, but is called out due to an emergency. Thus, the medical professional connects an inter-locking circuit cap to the devices described herein. The inter-locking circuit cap is connected to the device as a safety feature while the medical professional leaves the room to attend to the emergency. The inter-locking circuit cap prevents the UV light from being emitted prematurely. The inter-locking circuit cap has an RFID chip configured to allow the inter-locking circuit cap and device to communicate once the inter-locking circuit cap is connected to the devices described herein.

After the emergency is over the medical professional comes back into the patient's recovery room. The medical professional now removes the bags. Prior to attaching new bags, the medical professional uses the devices described herein to sterilize the surface of the connection ports. The medical professional removes the inter-locking circuit cap, thus removing the safety feature. Then, the medical professional inserts the device into one/the first connection port and switches on the device. The LED indicator lights start illuminating red incrementally. After about five seconds the red LED indicator lights turn off, and the LED indicator lights turn green. The green LED indicator lights signal to the medical professional that surface of the connection port is sterilized. The medical professional attaches a sterile port cap to the connection port to keep it sterile while she sterilizes the remaining connection ports. After the sterilization of each connection port she connects a sterile port cap to the connection port. Once the medical professional has completed sterilizing all the connection ports she begins hooking up the new bags. She first removes one port cap and hooks up the new bag. This is repeated until are three bags are up. The IV bag change is then complete.

Example 5

MRSA is plated onto twelve tryptic soy agar plates and incubated for 48 hours. Three of the plates are used as controls. The remaining plates were individually placed into UV devices and subjected to one second, three second, and seven seconds of exposure to UV light. All tests were performed in triplicate.

The plates exposed to 1 second of UV light exposure had a 99.99% kill. The plates exposed to 3 seconds of UV light exposure had a 99.996% kill. The plates exposed to 7 seconds of UV light exposure had a >99.99999% kill.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A sterilization device comprising:

a body comprising at least one indicator light, a battery, an optical sensor, and a light source; and an adapter cap comprising a lens and an RFID chip wherein the RFID chip is configured to allow communication between the adapter cap and the body;

wherein the body and the adapter cap are connected in a manner so that only the adapter cap includes an aperture configured to accept a luminal connection port; and wherein the adapter cap does not include a light source.

2. The sterilization device of claim 1, wherein the battery is at least 6 volts.

3. The sterilization device of claim 1, wherein the connection between the adapter cap and the luminal connection port is a threaded connection.

4. The sterilization device of claim 1, wherein the at least one indicator light turns green after the luminal connection port is sterilized.

5. The sterilization device of claim 1, wherein the light source is a light emitting diode.

6. The sterilization device of claim 1, wherein the light source emits ultraviolet C light.

7. The sterilization device of claim 1, wherein the light source has a wavelength of about 275 nm.

8. The sterilization device of claim 1, wherein the light source has a power of about 30 mW.

9. A sterilization device comprising:

a body comprising at least one indicator light, a battery, an optical sensor, and a light source;

a threaded adapter cap including a lens, and a clear substrate that irreversibly changes color indicating the completion of the sterilization; and an inter-locking circuit connected to the threaded adapter cap wherein the threaded adapter cap is configured to accept a luminal connection port;

wherein the body and the adapter cap are connected in a manner so that only the adapter cap includes an aperture configured to accept a luminal connection port; and wherein the adapter cap does not include a light source.

10. The sterilization device of claim 9, wherein the battery is at least 6 volts.

11. The sterilization device of claim 9, wherein the at least one indicator light turns green after the luminal connection port is sterilized.

12. The sterilization device of claim 9, wherein the light source emits ultraviolet C light.

13. The sterilization device of claim 9, wherein the light source has a wavelength of about 275 nm.

14. The sterilization device of claim 9, wherein the light source has a power of about 30 mW.

15. The sterilization device of claim 9, further including a switch, at least one or more sensors, or a multi-sensor to activate the sterilization device.

16. The sterilization device of claim 9, wherein sterilization occurs in less than about 10 sec.

17. The sterilization device of claim 9, wherein sterilization occurs in less than about 5 sec.

18. The sterilization device of claim 9, wherein microbial reduction is a 7-log microbial reduction.

19. The sterilization device of claim 9, wherein the clear substrate changes colors at different wavelengths.

20. The sterilization device of claim 9, wherein when the adapter cap is exposed to UV light the clear substrate changes color.

21. The sterilization device of claim 9, wherein the inter-locking circuit is configured to turn on a safety feature.

22. The sterilization device of claim 9, wherein the inter-locking circuit includes an RFID chip configured to allow the inter-locking circuit and body to communicate.

23. The sterilization device of claim 1, wherein the light source is a focal length from the adapter cap.

24. The sterilization device of claim 23, wherein the focal length is between about 5 mm and about 15 mm.

25. The sterilization device of claim 9, wherein the light source is a focal length from the threaded adapter cap.

26. The sterilization device of claim 25, wherein the focal length is between about 5 mm and about 15 mm.

* * * * *